United States Patent
Homma

(10) Patent No.: US 10,852,526 B2
(45) Date of Patent: Dec. 1, 2020

(54) OBJECTIVE OPTICAL SYSTEM AND ENDOSCOPE APPARATUS USING THE SAME

(71) Applicant: OLYMPUS CORPORATION, Hachioji (JP)

(72) Inventor: Hiroyuki Homma, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 112 days.

(21) Appl. No.: 16/212,184

(22) Filed: Dec. 6, 2018

(65) Prior Publication Data

US 2019/0113739 A1    Apr. 18, 2019

Related U.S. Application Data

(63) Continuation of application No. PCT/JP2017/019032, filed on May 22, 2017.

(30) Foreign Application Priority Data

Jun. 17, 2016    (JP) .................................. 2016-120716

(51) Int. Cl.
G02B 5/30     (2006.01)
G02B 23/24    (2006.01)
(Continued)

(52) U.S. Cl.
CPC ...... *G02B 23/2446* (2013.01); *A61B 1/00096* (2013.01); *A61B 1/00186* (2013.01);
(Continued)

(58) Field of Classification Search
CPC .............. G02B 5/3083; G02B 23/2446; G02B 27/283; A61B 1/00096; A61B 1/00163; A61B 1/00186; A61B 1/0638
(Continued)

(56) References Cited

U.S. PATENT DOCUMENTS 5,122,895 A * 6/1992 Takanashi ............ G02B 27/283
                                                    359/247
5,381,278 A * 1/1995 Shingaki .............. G02B 27/283
                                                    348/E9.027
(Continued)

FOREIGN PATENT DOCUMENTS

JP    2014103597 A     6/2014
WO    2013027459 A1    2/2013
(Continued)

OTHER PUBLICATIONS

International Search Report (ISR) dated Aug. 15, 2017 issued in International Application No. PCT/JP2017/019032.
(Continued)

*Primary Examiner* — Ricky D Shafer
(74) *Attorney, Agent, or Firm* — Holtz, Holtz & Volek PC

(57) ABSTRACT

An objective optical system includes a lens group and an optical-path splitting element. The optical-path splitting element has an optical-path splitting surface which forms a first optical path and a second optical path. A reflecting surface is positioned in the second optical path and a predetermined optical surface is positioned in the second optical path. A wavelength band of light transmitted through the predetermined optical surface or a wavelength band of light reflected at the predetermined optical surface is restricted. The wavelength band which is restricted is narrower than a wavelength band of light that travels along the other optical path. A quarter-wave plate is positioned between the optical-path splitting surface and the reflecting surface. The optical-path splitting surface has a characteristic of transmitting P-polarized light and reflecting S-polarized light. The predetermined optical surface is positioned between the optical-path splitting surface and the quarter-wave plate.

2 Claims, 6 Drawing Sheets

(51) Int. Cl.
*A61B 1/00* (2006.01)
*A61B 1/06* (2006.01)
*A61B 1/05* (2006.01)
*A61B 1/04* (2006.01)
*G02B 27/28* (2006.01)

(52) U.S. Cl.
CPC .............. *A61B 1/043* (2013.01); *A61B 1/051* (2013.01); *A61B 1/0638* (2013.01); *G02B 5/3083* (2013.01); *G02B 23/2484* (2013.01); *G02B 27/283* (2013.01); *A61B 1/00163* (2013.01)

(58) Field of Classification Search
USPC .............................. 359/489.07; 600/181, 183
See application file for complete search history.

(56) References Cited

U.S. PATENT DOCUMENTS

| | | | | |
|---|---|---|---|---|
| 5,387,991 | A * | 2/1995 | Mitsutake | G02B 27/283 349/1 |
| 5,434,669 | A * | 7/1995 | Tabata | A61B 1/042 356/241.5 |
| 5,446,510 | A * | 8/1995 | Mitsutake | G02B 27/283 348/E9.027 |
| 7,339,735 | B2 * | 3/2008 | Li | G02B 6/4298 349/9 |
| 8,684,914 | B2 | 4/2014 | Mcdowall et al. | |
| 2005/0277810 | A1 * | 12/2005 | Irion | A61B 1/0669 600/178 |
| 2013/0235174 | A1 | 9/2013 | Namii | |
| 2015/0002646 | A1 | 1/2015 | Namii | |
| 2015/0309284 | A1 | 10/2015 | Kagawa et al. | |
| 2017/0187943 | A1 | 6/2017 | Tsuyuki et al. | |

FOREIGN PATENT DOCUMENTS

WO 2014171284 A1 10/2014
WO 2016043107 A1 3/2016

OTHER PUBLICATIONS

Written Opinion dated Aug. 15, 2017 issued in International Application No. PCT/JP2017/019032.
International Preliminary Report on Patentability (IPRP) (and English language translation thereof) and Written Opinion dated Dec. 27, 2018 issued in counterpart International Application No. PCT/JP2017/019032.
Chinese Office Action (and English language translation thereof) dated Sep. 3, 2020 issued in counterpart Chinese Application No. 201780035383.8.

* cited by examiner

OBJECTIVE OPTICAL SYSTEM AND ENDOSCOPE APPARATUS USING THE SAME

CROSS-REFERENCE TO RELATED APPLICATION

The present application is a continuous application of PCT/JP2017/019032 filed on May 22, 2017 which is based upon and claims the benefit of priority from Japanese Patent Application No. 2016-120716 filed on Jun. 17, 2016; the entire contents of which are incorporated herein by reference.

BACKGROUND OF THE INVENTION

Field of the Invention

The present invention relates to an objective optical system and an endoscope apparatus using the same.

Description of the Related Art

As a method of observation in endoscopes, a white light observation and a narrow-band light observation are available. In the white light observation, an object is illuminated by white light. Transmission of light and reflection of light occur at the object. A wavelength band of light transmitted through the object and light intensity at each wavelength differ according to optical characteristics of the object. Even a wavelength of light reflected at the object and light intensity at each wavelength differ according to optical characteristics of the object. In the white light observation, an optical image is formed by light of all wavelength bands, and the observation is carried out by using the optical image.

In the narrow-band light observation, either an object is illuminated by light of a narrow wavelength band or the illumination is carried out by the white light. In the former case, an optical image is formed by light of all wavelength bands similarly as in a normal observation, and the observation is carried out by using the optical image. In the latter case, an optical image is formed by light of a wavelength band narrower than the wavelength band of the white light, and the observation is carried out by using the image. Therefore, an optical filter is disposed on an object side of the optical image for instance, and only light of a narrow wavelength band is either transmitted or reflected by the optical filter.

Optical systems which form two optical images from one objective optical system are disclosed in U.S. Pat. No. 8,684,914 Specification, International Unexamined Patent Application Publication No. 2013/027459, and Japanese Patent Application Laid-open Publication No. 2014-103597.

In U.S. Pat. No. 8,684,914 Specification, a stereoscopic endoscope which includes two image pickup units has been disclosed. Each image pickup unit includes a lens assembly and a sensor assembly. An optical image of an object is formed by the lens assembly.

The sensor assembly includes a prism assembly, a reflector unit, and two image pickup sensors. The prism assembly includes a first surface (beam splitting surface) and a second surface (reflecting surface).

In the sensor assembly, light is divided into two at the beam splitting surface. Accordingly, a first optical path and a second optical path are formed. As a result, a first optical image is formed on the first optical path and a second optical image is formed on the second optical path. The first optical image and the second optical image are formed at different positions on the same plane.

A first image pickup sensor is disposed on the first optical path. The first optical image is captured by the first image pickup sensor. A second image pickup sensor is disposed on the second optical path. The second optical image is captured by the second image pickup sensor.

In International Unexamined Patent Application Publication No. 2013/027459, an image pickup apparatus system which includes two optical paths has been disclosed. One of the optical paths is an optical path for a fluorescent observation, and has a first polarizing plate and an objective lens for fluorescent observation. The other optical path is an optical path for white light observation, and has a second polarizing plate and an objective lens for white light observation. The first polarizing plate and the second polarizing plate are disposed such that directions of polarization thereof are orthogonal.

One polarization beam splitter is disposed at a position where the two optical paths intersect. By the polarization beam splitter, one of fluorescent light and white light is reflected at a polarization beam splitter surface, and the other is transmitted through the polarization beam splitter. A fluorescent image and a white light image are formed at different positions in the same plane. The fluorescent image and the white light image are captured by one image pickup element.

In Japanese Patent Application Laid-open Publication No. 2014-103597, an image pickup apparatus which includes an objective optical system, a splitting element, and one image pickup element has been disclosed. In the image pickup apparatus, two optical images are formed by the splitting element, and the two optical images are captured by the image pickup element. The image pickup element has a first area for disposing a filter and a second area for disposing a filter.

SUMMARY OF THE INVENTION

An objective optical system according to at least some embodiments of the present invention comprises:

a lens group which forms an image of an object, and an optical-path splitting element which is disposed on an image side of the lens group, wherein the optical-path splitting element is disposed on an optical path of the lens group, and the optical-path splitting element has an optical-path splitting surface which forms a first optical path and a second optical path, and the first optical path is formed on an extended line of the optical path of the lens group, and the second optical path is formed to intersect the first optical path, and an optical image on the first optical path and an optical image on the second optical path are formed on the same plate, and a reflecting surface is positioned in the second optical path, and a predetermined optical surface is positioned in only the second optical path, and a wavelength band of light transmitted through the predetermined optical surface or a wavelength band of light reflected at the predetermined optical surface is restricted, and the wavelength band which is restricted is narrower than a wavelength band of light that travels along the other optical path, and a quarter-wave plate is positioned between the optical-path splitting surface and the reflecting surface, and the optical-path splitting surface has a characteristic of transmitting P-polarized light and reflecting S-polarized light, and the predetermined optical surface is positioned between the optical-path splitting surface and the quarter-wave plate.

Moreover, an endoscope apparatus of the present invention comprises, the abovementioned objective optical system, an image pickup element, and an image processing unit.

DETAILED DESCRIPTION OF THE INVENTION

Figure 1:
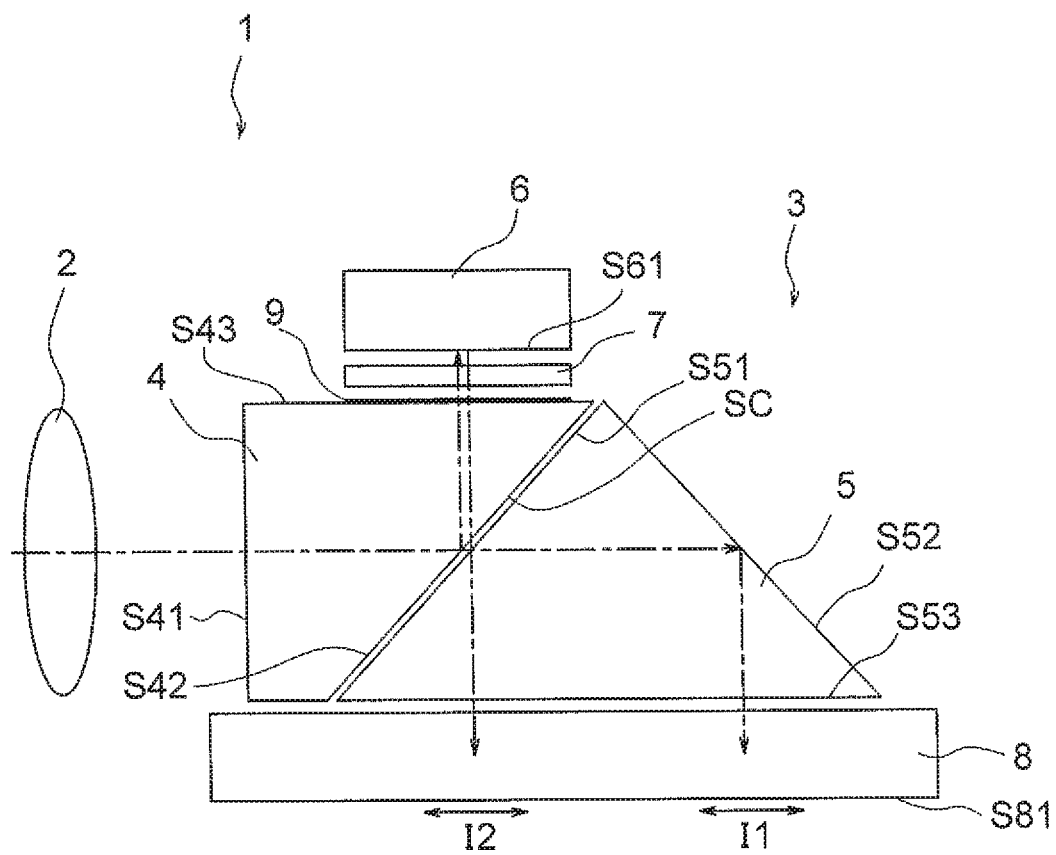
FIG. 1 is a diagram showing an arrangement of an objective optical system of the present embodiment.

Reasons for and an effect of adopting such arrangements for an objective optical system according to the present embodiment and an endoscope apparatus according to the present embodiment will be described below by using the accompanying diagrams. However, the present invention is not restricted by the objective optical system according to the present embodiment and the endoscope apparatus according to the present embodiment.

An objective optical system of the present embodiment includes a lens group which forms an image of an object, and an optical-path splitting element which is disposed on an image side of the lens group, wherein the optical-path splitting element is disposed on an optical path of the lens group, and the optical-path splitting element has an optical-path splitting surface which forms a first optical path and a second optical path, and the first optical path is formed on an extended line of the optical path of the lens group, and the second optical path is formed to intersect the first optical path, and an optical image on the first optical path and an optical image on the second optical path are formed on the same plane, and a reflecting surface is positioned in the second optical path, and a predetermined optical surface is positioned in only one of the first optical path and the second optical path, and a wavelength band of light transmitted through the predetermined optical surface or a wavelength band of light reflected at the predetermined optical surface is restricted, and the wavelength band which is restricted is narrower than a wavelength band of light that travels along the other optical path.

The objective optical system of the present embodiment includes the optical-path splitting element which is disposed on the image side of the lens group. The optical-path splitting element has the optical-path splitting surface. A surface having polarization characteristics and a half-mirror surface are examples of the optical-path splitting surface.

In a case in which the optical-path splitting surface has the polarization characteristics, a quarter-wave plate is disposed in the optical path. In a case in which the optical-path splitting surface is a half-mirror surface, it is not necessary to dispose the quarter-wave plate. A case in which the optical-path splitting surface has the polarization characteristics will be described below.

The first optical path and the second optical path are formed by the optical-path splitting surface. The predetermined optical surface is positioned in only one of the first optical path and the second optical path. Transmission of light or reflection of light occurs at the predetermined optical surface. However, the wavelength band of the light transmitted or the wavelength band of the light reflected is restricted.

An interference filter and a colored glass filter are examples of the element which restricts the wavelength band of light. The interference filter has an optical film which is formed on an optical surface. In the interference filter, light of a specific wavelength band is transmitted or reflected by the optical film. In the colored glass filter, light of a specific wavelength band is absorbed. The description will be made below by using the optical film.

In FIG. 1, an arrangement of the objective optical system of the present embodiment is shown. An objective optical system 1 includes a lens group 2 and an optical-path splitting unit 3. The lens group 2 includes a plurality of lenses. However, in FIG. 1, the lens group 2 is indicated by one lens. An optical image of an object is formed by the lens group 2.

The optical-path splitting unit 3 is disposed on the image side of the lens group 2. The optical-path splitting unit 3 includes a prism 4, a prism 5, a mirror 6, a quarter-wave plate 7, and a cover glass 8. The prism 4 is a trapezoidal prism and the prism 5 is a triangular prism. The optical-path splitting element is formed by the prism 4 and the prism 5. The optical-path splitting element is a polarization beam splitter.

The prism 4 is cemented to the prism 5. A cemented surface SC is formed by an optical surface S42 of the prism 4 and an optical surface S51 of the prism 5. The cemented surface SC has a characteristic of transmitting P-polarized light and reflecting S-polarized light.

The mirror 6 is disposed such that an optical surface S61 is facing an optical surface S43 of the prism 4. The cover glass 8 is cemented to an optical surface S53 of the prism 5.

The optical-path splitting unit 3 is disposed in the optical path of the lens group 2. Light emerged from the lens group 2 (hereinafter, referred to as 'image forming light') is incident on the optical-path splitting unit 3. In the optical-path splitting unit 3, an optical surface S41 is positioned nearest to the lens group 2. Therefore, the image forming light is incident on the optical surface S41. The optical surface S41 being a transmitting surface, the image forming light is transmitted through the optical surface S41.

Next, the image forming light is incident on the cemented surface SC. The cemented surface SC is disposed such that a normal of a plane is at 45 degrees with respect to an optical axis. The image forming light incident on the cemented surface SC is divided into light transmitted through the cemented surface SC (hereinafter, referred to as 'image forming light 1') and light reflected at the cemented surface SC (hereinafter, referred to as 'image forming light 2').

As mentioned above, the optical-path splitting element is a polarization beam splitter. Therefore, at the cemented surface SC, the P-polarized light is transmitted through, and the S-polarized light is reflected. The image forming light 1 becomes the P-polarized light and the image forming light 2 becomes the S-polarized light.

The image forming light 1 and the image forming light 2 travel in mutually different directions. When an optical path along which the image forming light 1 travels is let to be a first optical path and an optical path along which the image forming light 2 travels is to be a second optical path, the first optical path and the second optical path are formed by the cemented surface SC. Thus, the cemented surface SC is the optical-path splitting surface.

The first optical path is formed on an extended line of the optical path of the lens group 2. The second optical path is formed to intersect the first optical path. In FIG. 1, the second optical path is orthogonal to the first optical path.

In the first optical path, the cemented surface SC, an optical surface S52, the optical surface S53, and an optical surface S81 are positioned.

The image forming light 1 is incident on the optical surface S52. The optical surface S52 is a reflecting surface. The image forming light 1 is reflected at the optical surface S52 and is incident on the optical surface S53. The optical surface S53 is a transmitting surface. The image forming light 1 is transmitted through the optical surface S53 and is incident on the cover glass 8. The image forming light 1 reaches the optical surface S81. The optical surface S81 is a transmitting surface. An optical image I1 is formed near the optical surface S81.

In the second optical path, the cemented surface SC, the optical surface S43, the quarter-wave plate 7, the optical surface S61, the optical surface S53, and the optical surface S81 are positioned.

The image forming light 2 is incident on the optical surface S43. The optical surface S43 is a transmitting surface. The image forming light 2 is transmitted through the optical surface S43 and the quarter-wave plate 7, and is incident on the optical surface S61 of the mirror 6. The optical surface S61 is a reflecting surface. The image forming light 2 is reflected at the optical surface S61, and upon being transmitted through the quarter-wave plate 7, is incident on the optical surface S43.

The quarter-wave plate 7 is disposed in the second optical path. The image forming light 2 is linearly-polarized light. The image forming light 2, by passing through the quarter-wave plate 7, is converted to circularly-polarized light. The image forming light 2 is reflected at the optical surface S61 of the mirror 6, and passes again through the quarter-wave plate 7.

The image forming light 2, by passing through the quarter-wave plate 7, is converted to linearly-polarized light. In the image forming light 2 emerged from the quarter-wave plate 7, a direction of polarization becomes a direction orthogonal to an S-direction. In other words, the image forming light 2 becomes P-polarized light. Therefore, the image forming light 2 is transmitted through the cemented surface SC.

The image forming light transmitted through the cemented surface SC is incident on the optical surface S53. The image forming light 2 is transmitted through the optical surface S53 and is incident on the cover glass 8. The image forming light 2 reaches the optical surface S81. An optical image I2 is formed near the optical surface S81.

An optical path length is substantially same for the first optical path and the second optical path. Therefore, the optical image I1 and the optical image I2 are formed on the same plane.

Figure 2:
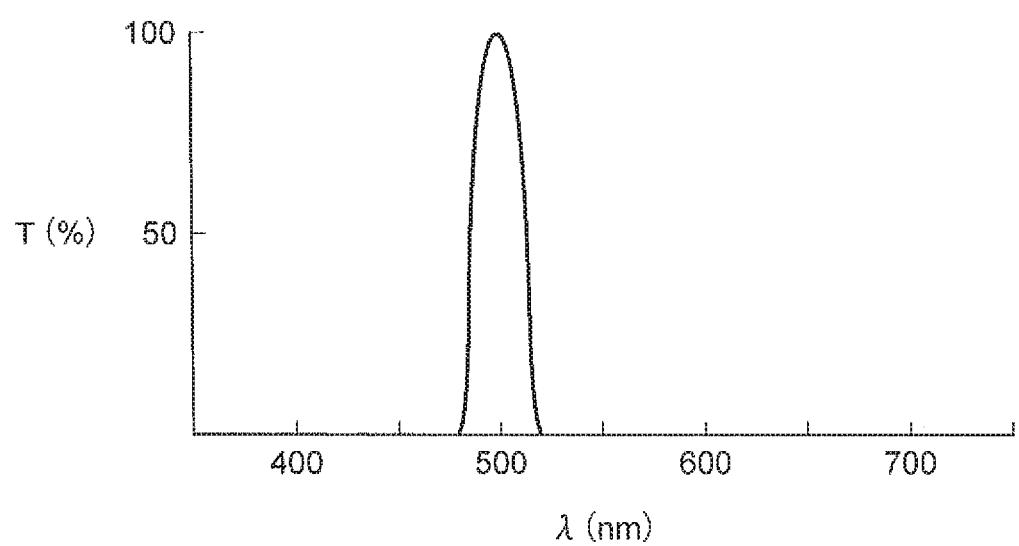
FIG. 2 is a diagram showing spectral characteristics of an optical film.

In the objective optical system of the present embodiment, an optical film 9 is provided to the optical surface S43. FIG. 2 is a diagram showing spectral characteristics of the optical film 9. The spectral characteristics are characteristics in which a transmittance or a reflectance at the optical surface is indicated as a function of wavelength. In FIG. 2, the spectral characteristics of the transmittance are shown.

As shown in FIG. 2, in the optical film 9, for a wavelength band from 480 nm to 520 nm, the transmittance is 1% or more and 100% or less. On a side of wavelength shorter than 480 nm and on a side of wavelength longer than 520 nm, the transmittance is 1% or less.

Let an object be illuminated by white light such as light of wavelength band from 400 nm to 700 nm. Moreover, let a wavelength band of light reflected at the object be almost same as the wavelength band of the illumination light. In this case, light of the wavelength band from 400 nm to 700 nm is incident on the lens group 2 from the object. Therefore, the wavelength band of the image forming light becomes 400 nm to 700 nm.

The image forming light is incident on the cemented surface SC, and is split into the image forming light 1 and the image forming light 2. The image forming light 1 travels along the first optical axis. The image forming light 2 travels along the second optical axis. The optical surface S43 provided with the optical film 9 is positioned in the second optical path. The image forming light 2 is incident on the optical surface S43.

Figure 3:
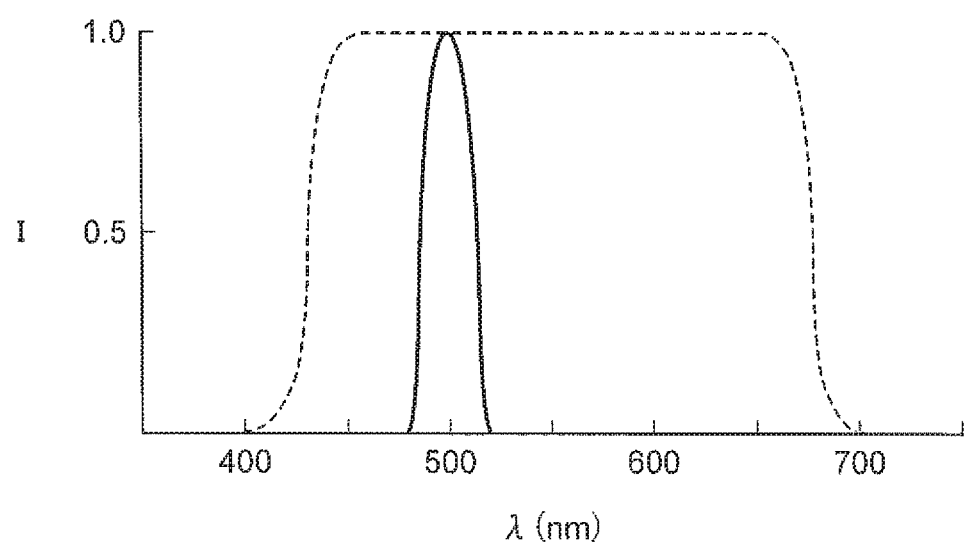
FIG. 3 is a diagram showing a distribution of light intensity.

FIG. 3 is a diagram showing a distribution of intensity of light. In FIG. 3, the distribution of intensity of light passed through the optical surface S42 is shown by a solid line. The distribution of intensity of light advancing along the first optical path is shown by a dashed line. A vertical axis indicates the intensity of light and a horizontal axis indicates the wavelength. The intensity of light is normalized by the maximum value of light advancing along the first optical path.

The optical film 9 does not exist in the first optical path. Therefore, as shown by the dashed line in FIG. 3, the wavelength band of the image forming light is from 400 nm to 700 nm. In such manner, a width of the wavelength band of the image forming light 1 is almost same as a width of the wavelength band of the image forming light.

The optical film 9 does exist in the second optical path. The wavelength band of the image forming light before being incident on the optical surface S43, similarly as the wavelength band of the image forming light 1, is from 400 nm to 700 nm.

However, while passing through the optical surface S43, only light of the wavelength band from 480 nm to 520 nm is transmitted through the optical film 9, and light of a wavelength band shorter than 480 nm and light of a wavelength band longer than 520 nm are reflected at the optical film 9. Therefore, a width of the wavelength band of the image forming light 2 after emerging from the optical surface S43, as shown by the solid line in FIG. 3, is from 480 nm to 520 nm.

In such manner, the objective optical system of the present embodiment has the optical surface S43 provided with the optical film 9, as the predetermined optical surface. Therefore, the wavelength band of the light transmitted through the optical surface S43 is restricted. The optical surface S43 being positioned only in the second optical path, the wavelength band of the light transmitted through the optical surface S43 becomes narrower than the wavelength band of the image forming light 1 that travels along the first optical path.

As mentioned above, the wavelength band of the image forming light 1 is from 400 nm to 700 nm. Therefore, the optical image I1 is formed by the light of the wavelength band from 400 nm to 700 nm, or in other words, by white light. By observing the optical image I1, it is possible to carry out white light observation.

On the other hand, the wavelength band of the image forming light 2 emerging from the optical surface S43 is from 480 nm to 520 nm. Therefore, the optical image I2 is formed by the light of wavelength band from 480 nm to 520 nm, or in other words, by narrow-band light. By observing the optical image I2, it is possible to carry out narrow-band light observation.

In the objective optical system of the present embodiment, the number of optical paths formed on the object side of the optical-path splitting unit 3 is one. Therefore, it is possible to make the objective optical system small-sized. Moreover, since the optical image I1 and the optical image I2 are formed simultaneously, it is possible to carry out the white light observation and the narrow-band light observation simultaneously.

Moreover, a wavelength band of the light forming the optical image I1 and a wavelength band of the light forming the optical image I2 differ. Therefore, in a case of capturing the optical image I1 and the optical image I2 by an image pickup element, it is possible to make a color filter of a region to be captured with the optical image I1 and a color filter of a region to be captured with the optical image I2 the same. As a result, it is possible to use an image pickup element which is highly versatile.

In such manner, according to the objective optical system of the present embodiment, it is possible to realize an objective optical system which is capable of carrying out simultaneously the white light observation and the narrow-band light observation using a highly versatile image pickup element, while being a small-sized optical system.

In the objective optical system shown in FIG. 1, the optical film 9 is provided to the optical surface S43. However, a plane parallel plate may be disposed between the optical surface S43 and the quarter-wave plate, and the optical film 9 may be provided to a surface of the plane parallel plate. Moreover, a colored glass filter may be disposed between the optical surface S43 and the quarter-wave plate 7.

In the objective optical system of the present embodiment, it is preferable that the predetermined optical surface be positioned in the second optical path, and the quarter-wave plate be positioned between the optical-path splitting surface and the reflecting surface, and the optical-path splitting surface have a characteristic of transmitting P-polarized light and reflecting S-polarized light, and the predetermined optical surface be positioned between the optical-path splitting surface and the quarter-wave plate.

The image forming light 2 directed toward the optical surface S43 from the optical-path splitting surface, or in other words, from the cemented surface SC, is S-polarized light. A case in which the quarter-wave plate 7 has not been disposed between the cemented surface SC and the optical surface S61 will be described below.

In this case, the image forming light 2, up on passing through the optical surface S43, is reflected at the optical surface S61. The image forming light 2, after passing again through the optical surface S43, is incident on the cemented surface SC. The image forming light 2 immediately before being incident on the cemented surface SC is S-polarized light. At the cemented surface SC, the S-polarized light is reflected. Therefore, the image forming light 2 is reflected at the cemented surface SC, and is directed toward the lens group 2. In this case, it is not possible to form the optical image I1.

In the objective optical system of the present embodiment, the quarter-wave plate 7 is disposed between the cemented surface SC and the optical surface S61. Accordingly, the image forming light 2 immediately before being incident on the cemented surface SC becomes P-polarized light. Therefore, the image forming light 2 passes through all the cemented surfaces SC. In other words, an intensity of the image forming light 2 becomes same before and after passing through the cemented lens SC.

As mentioned later, it is possible to make the cemented surface SC a half-mirror surface. Even in this case, the image forming light 2, after passing through the optical surface S43, is reflected at the optical surface S61, and is incident on the cemented surface SC. However, the cemented surface SC being the half-mirror surface, the intensity of the image forming light 2 after passing through the cemented surface SC becomes half of the intensity before passing through the cemented surface SC.

At the same time, in the objective optical system of the present embodiment, as mentioned above, the intensity of the image forming light 2 is same before and after passing through the cemented surface SC. Therefore, it is possible to suppress lowering of the intensity of the image forming light as compared to the case in which the cemented surface is the half-mirror surface.

Moreover, it is preferable that the predetermined optical surface, or in other words, an optical surface provided with the optical film 9, be positioned between the cemented surface SC and the quarter-wave plate 7. In the objective optical system of the present embodiment, the optical surface S43 is positioned between the cemented surface SC and the quarter-wave plate 7. Therefore, the optical film 9 is provided to the optical surface S43.

As mentioned above, for the optical film 9, light of a wavelength band from 480 nm to 520 nm (hereinafter, referred to as 'image forming light 2T') passes through the optical film 9. The image forming light 2T, upon passing through the quarter-wave plate 7, is reflected at the optical surface S61, and passes again through the quarter-wave plate 7. Moreover, the image forming light 2T is transmitted once again through the optical film 9 and is incident on the cemented surface SC.

Whereas, light of a wavelength band shorter than 480 nm and light of wavelength band longer than 520 nm (hereinafter, referred to as 'image forming light 2R') are reflected at the optical film 9. The image forming light 2R reflected at the optical film 9 is incident on the cemented surface SC. Accordingly, the image forming light 2T and the image forming light 2R are incident on the cemented surface SC.

The image forming light 2T is light in which S-polarized light passed twice through the quarter-wave plate 7. Therefore, image forming light 2T is P-polarized light. Consequently, the image forming light 2T is transmitted through the cemented surface SC. Moreover, the optical image I2 is formed by the image forming light 2T. The optical image I2 is formed by light of wavelength band from 480 nm to 520 nm, or in other words, by narrow-band light.

Whereas, the image forming light 2R is light in which S-polarized light reflected at the optical film 9. Therefore, the image forming light 2R is reflected at the cemented surface SC. Since the image forming light 2R travels toward the lens group 2, the image forming light 2R does not contribute to formation of the optical image I2.

In such manner, by the optical surface provided with the optical film 9 being positioned between the cemented surface SC and the quarter-wave plate 7, is it possible to form only an optical image by the narrow-band light.

In a case in which the optical surface provided with the optical film 9 is positioned between the quarter-wave plate 7 and the optical surface S61, the image forming light 2R also becomes the light in which S-polarized light passed twice through the quarter-wave plate. In this case, the image forming light 2R is also transmitted through the cemented surface together with the image forming light 2T. A wavelength band of light in which the image forming light 2R and the image forming light 2T are combined is same as the wavelength band of the white light. Therefore, the optical image I2 becomes an optical image by the white light.

For such reason, it is not preferable that the optical surface provided with the optical film 9 be positioned between the quarter-wave plate and the optical surface S61.

In the objective optical system of the present embodiment, it is preferable that the predetermined optical surface be insertable in and extractable from the second optical path.

As mentioned above, the plane parallel plate may be disposed between the optical surface S43 and the quarter-wave plate 7, and the optical film 9 may be provided to the surface of the plane parallel plate. Moreover, a colored glass filter may be used instead of the plane parallel plate provided with the optical film 9.

Moreover, the plane parallel plate provided with the optical film 9 may be let to be insertable into and extractable from the second optical path. In a case in which the plane parallel plate is inserted into the second optical path, the optical image I1 is formed by the white light, and the optical image I2 is formed by the narrow-band light. An optical path length of the first optical path and an optical path length of the second optical path are equal. Therefore, a focused region is same for the optical image I1 and the optical image I2. Therefore, it is possible to carry out the white light observation and the narrow-band light observation simultaneously.

Whereas in a case in which the plane parallel plate is extracted out from the second optical path, the optical image I1 and the optical image I2 are formed by the white light. Therefore, it is possible to carry out the white light observation but it is not possible to carry out the narrow-band light observation.

Furthermore, in the case in which the plane parallel plate is extracted out from the second optical path, the optical path length of the first optical path and the optical path length of the second optical path differ. Therefore, a focused region differs for the optical image I1 and the optical image I2. Such optical image I1 and optical image I2 are captured, and accordingly two images are acquired. Moreover, only the focused region is extracted from the two images captured, and the regions extracted are combined. By doing so, it is possible to acquire an image with a large depth of field.

In the objective optical system of the present embodiment, it is preferable that the predetermined optical surface be positioned in the first optical path, and the optical-path splitting surface be a half-mirror surface.

In the objective optical system of the present embodiment, the cemented surface SC is a half-mirror surface. In this case, the predetermined optical surface is positioned in the first optical path. More specifically, the optical surface S52 is provided with the optical film 9.

The image forming light is incident on the cemented surface SC, and is divided into the image forming light 1 and the image forming light 2. The image forming light 1 travels along the first optical path. The image forming light 2 travels along the second optical path. The optical surface S52 provided with the optical film 9 is positioned in the first optical path. The image forming light 1 is incident on the optical surface S52.

The wavelength band of the image forming light before being incident on the optical surface S52 is from 400 nm to 700 nm. However, at the time of passing through the optical surface S52, only light of the wavelength band from 480 nm to 520 nm is reflected at the optical film 9.

Whereas, light of wavelength band shorter than 480 nm and light of wavelength band longer than 520 nm passes through the optical film 9. Therefore, the wavelength band of the image forming light 1 emerged from the optical surface S52 is 480 nm to 520 nm.

The optical film 9 does not exist in the second optical path. Therefore, the wavelength band of the image forming light 2 is from 400 nm to 700 nm. A width of the wavelength band of the image forming light 2 is almost same as a width of the wavelength band of the image forming light.

In such manner, the objective optical system of the present embodiment has the optical surface provided with the optical film 9 as the predetermined optical surface. Moreover, the optical surface provided with the optical film 9 is positioned only in the first optical path. Therefore, the wavelength band of light at the optical surface provided with the optical film 9 is narrower than the wavelength band of the image forming light 2 that travels along the second optical path.

As mentioned above, the wavelength band of the image forming light 1 emerged from the optical surface S52 is from 480 nm to 520 nm. Therefore, the optical image I1 is formed by the light of the wavelength band from 480 nm to 520 nm, or in other words, the narrow-band light. By observing the optical image I1, it is possible to carry out the narrow-band light observation.

Whereas, the wavelength band of the image forming light 2 is from 400 nm to 700 nm. Therefore, the optical image I2 is formed by the light of wavelength band from 400 nm to 700 nm, or in other words, the white light. By observing the optical image I2, it is possible to carry out the white light observation.

In the objective optical system of the present embodiment, the polarization has not been used. Therefore, it is not necessary to dispose the quarter-wave plate 7 in the second optical path. Therefore, it is possible to make the optical system small-sized.

Moreover, by making the optical surface S43 a reflecting surface, the mirror 6 becomes unnecessary. Therefore, it is possible to make the optical system further small-sized. In a case of making the optical surface S43 a reflecting surface, a size of the prism 4 and the prism 5 is to be set such that the optical path length of the first optical path and the optical path length of the second optical path become equal.

In the objective optical system of the present embodiment, it is preferable that the predetermined optical surface be provided with an optical film and the optical film have spectral characteristics of generating light of the restricted wavelength band, and the following conditional expression (1) be satisfied:

$$3 \text{ nm} \leq T\lambda \times \Delta\lambda \leq 60 \text{ nm} \tag{1}$$

where, $T\lambda$ denotes the maximum transmittance ($0 \leq T\lambda \leq 1.0$) in the restricted wavelength band, and $\Delta\lambda$ denotes a full width at half maximum of the restricted wavelength band (The unit is nm).

In a case of falling below a lower limit value of conditional expression (1), the optical image formed by the narrow-band light becomes excessively dark. Consequently, the observation with the narrow-band light becomes difficult. In a case of exceeding an upper limit value of conditional expression (1), the wavelength band at the predetermined optical surface becomes excessively wide. Consequently, an effect in the narrow-band light observation is degraded.

Highlighting of blood vessel is an example of the effect in the narrow-band light observation. More specifically, by using light of a wavelength band of blue color, it is possible to highlight a blood vessel positioned at a superficial layer. By using light of a wavelength band of green color, it is possible to highlight a blood vessel positioned at a mid-deep layer. Moreover, by using light of a wavelength band of red color, it is possible to highlight a thick blood vessel.

In the objective optical system of the present embodiment, it is preferable that the number of the restricted wavelength bands be in plurality, and each of the restricted wavelength bands satisfy the conditional expression (1).

By making such arrangement, it is possible to carry out the narrow-band light observation in the plurality of wavelength bands. Accordingly, since an amount of information related to object increases, it is possible improve accuracy of screening, diagnosis, and treatment.

Figure 4:
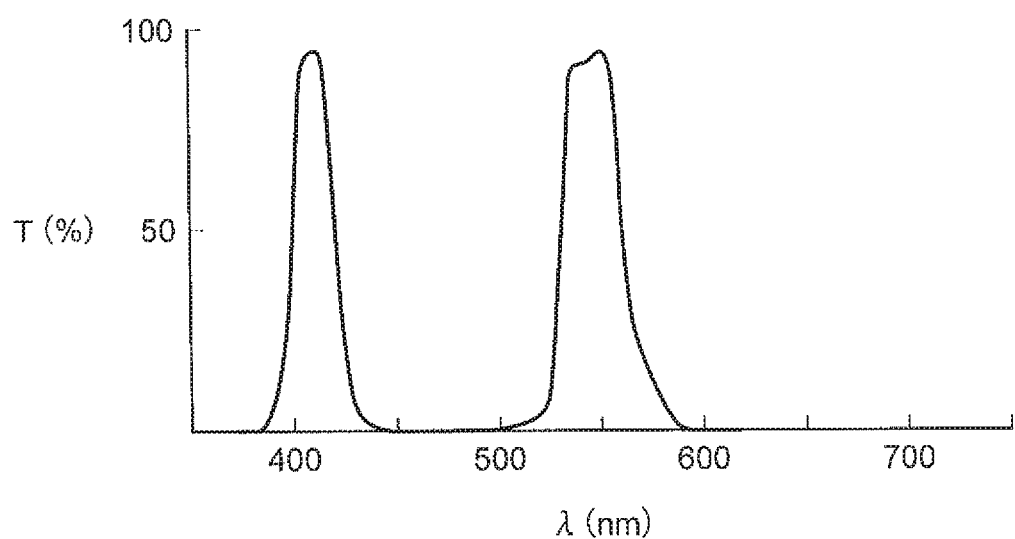
FIG. 4 is a diagram showing spectral characteristics of a band-pass filter of an example 1.

Examples of the plurality of restricted wavelength bands will be shown. FIG. 4 is a diagram showing spectral characteristics of a band-pass filter of an example 1. By using the band-pass filter of the example 1, it is possible to generate two lights of the restricted wavelength range.

The spectral characteristics of the band-pass filter of the example 1 have two restricted wavelength bands. More specifically, as shown in table 1, the spectral characteristics have a narrow band 1 and a narrow band 2. In table 1, $\lambda c$ denotes a central wavelength of a band, FWHM denotes a full width at half maximum, and Tmax denotes the maximum transmittance.

TABLE 1

| | Wavelength band | λc (nm) | FWHM (nm) | Tmax (%) | Effect |
|---|---|---|---|---|---|
| Narrow band 1 | blue light | 410 | 21 | 95 | highlighting superficial layer blood vessel |
| Narrow band 2 | green light | 545 | 30 | 95 | highlighting mid-deep layer blood vessel |

By using the band-pass filter of the example 1, it is possible to highlight a blood vessel positioned at a superficial layer and to highlight a blood vessel position at a mid-deep layer.

Figure 5:
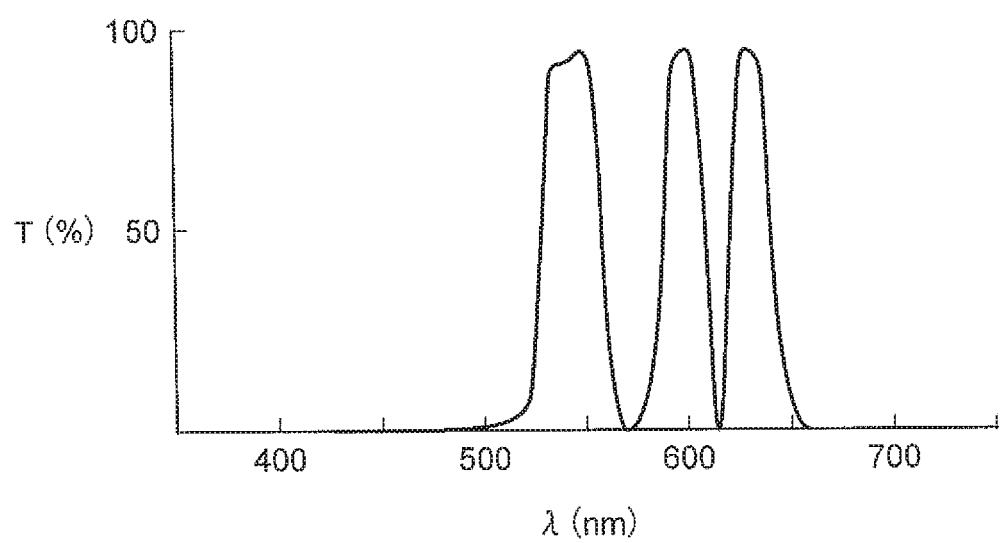
FIG. 5 is a diagram showing spectral characteristics of the optical film.

FIG. 5 is a diagram showing spectral characteristics of a band-pass filter of an example 2. By using the band-pass filter of the example 2, it is possible to generate three lights of restricted wavelength band.

The spectral characteristics of the band-pass filter of the example 2 have three restricted wavelength bands. More specifically, as shown in table 2, the spectral characteristics have the narrow band 2, a narrow band 3, and a narrow band 4.

TABLE 2

| | Wavelength band | λc (nm) | FWHM (nm) | Tmax (%) | Effect |
|---|---|---|---|---|---|
| Narrow band 2 | green light | 545 | 30 | 95 | highlighting mid-deep layer blood vessel |

TABLE 2-continued

| | Wavelength band | λc (nm) | FWHM (nm) | Tmax (%) | Effect |
|---|---|---|---|---|---|
| Narrow band 3 | red light | 600 | 20 | 95 | highlighting thick blood vessel |
| Narrow band 4 | red light | 630 | 20 | 95 | highlighting thick blood vessel |

By using the band-pass filter of the example 2, it is possible to highlight a blood vessel positioned at a mid-deep layer and to highlight a thick blood vessel.

An endoscope apparatus of the present embodiment includes the objective optical system of the present embodiment, an image pickup element, and an image processing unit.

Figure 6:
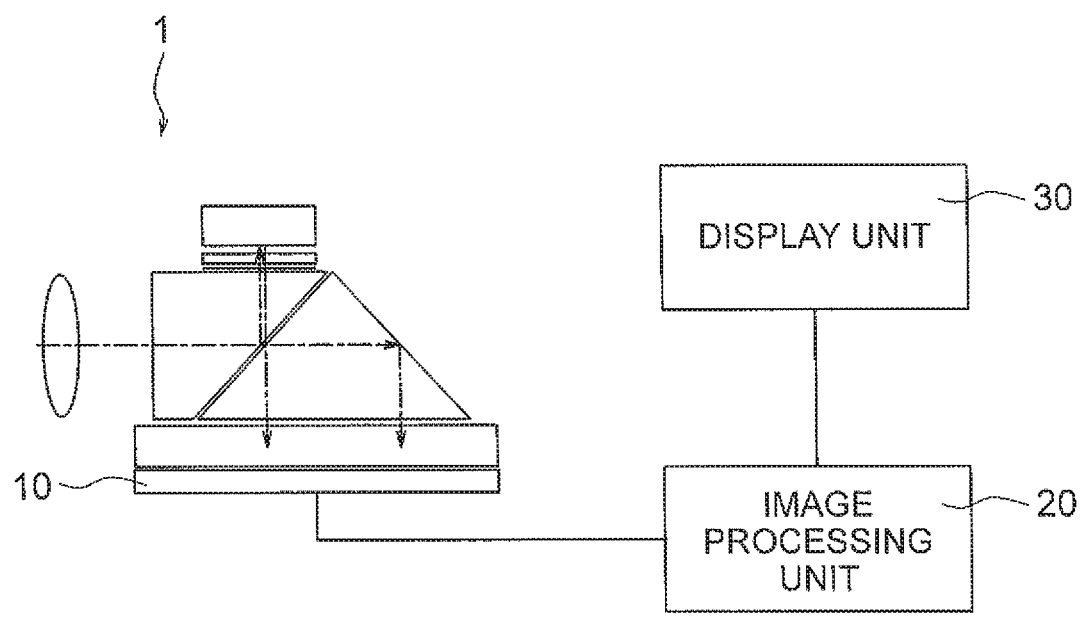
FIG. 6 is a diagram showing an arrangement of an endoscope apparatus of the present embodiment.

FIG. 6 is a diagram showing an arrangement of the endoscope apparatus of the present embodiment. The endoscope apparatus includes the objective optical system 1, an image pickup element 10, and an image processing unit 20. The endoscope apparatus may include a display unit 30.

As mentioned above, the optical image 1 and the optical image 2 are formed by the objective optical system 1. One of the two optical images is formed by the white light, and the other optical image is formed by the narrow-band light. The optical image 1 and the optical image 2 are captured by the image pickup element 10.

An image signal is output from the image pickup element 10. The image signal includes an image signal corresponding to the optical image 1 and an image signal corresponding to the optical image 2. The image signal output from the image pickup element 10 is input to the image processing unit 20. In the image processing unit 20, image processing is carried out on the image signal according to the requirement. The image signal is input to the display unit 30.

As mentioned above, the image signal includes the image signal corresponding to the optical image 1 and the image signal corresponding to the optical image 2. Therefore, a white light image and a narrow-band light image are displayed on the display unit 30.

According to the endoscope apparatus of the present embodiment, it is possible to carry out the narrow-band light observation and the white light observation simultaneously. Accordingly, since an amount of information related to object increases, it is possible to improve the accuracy of screening, diagnosis, and treatment.

Various embodiments of the present invention were described heretofore. However, the present invention is not restricted to the embodiments described, and embodiments in which the arrangements of the embodiments described are combined appropriately without departing from the scope of the invention also fall in the category of the present invention.

(Note)

An invention of the following arrangement is derived from the examples.

(Appended Mode 1)

An objective optical system, comprising:

a lens group which forms an image of an object; and an optical-path splitting element which is disposed on an image side of the lens group, wherein the optical-path splitting element is disposed on an optical path of the lens group, and the optical-path splitting element has an optical-path splitting surface which forms a first optical path and a second optical path, and the first optical path is formed on an extended line of the optical path of the lens group, and the second optical path is formed to intersect the first optical path, and an optical image on the first optical path and an optical image on the second optical path are formed on the same plane, and a reflecting surface is positioned in the second optical path, and a predetermined optical surface is positioned in only one of the first optical path and the second optical path, and a wavelength band of light transmitted through the predetermined optical surface or a wavelength band of light reflected at the predetermined optical surface is restricted, and the wavelength band which is restricted is narrower than a wavelength band of light that travels along the other optical path.

(Appended Mode 2)

The objective optical system according to appended mode 1, wherein the predetermined optical surface is positioned in the second optical path, and a quarter-wave plate is positioned between the optical-path splitting surface and the reflecting surface, and the optical-path splitting surface has a characteristic of transmitting P-polarized light and reflecting S-polarized light, and the predetermined optical surface is positioned between the optical-path splitting surface and the quarter-wave plate.

(Appended Mode 3)

The objective optical system according to one of appended modes 1 and 2, wherein the predetermined optical surface is insertable into and extractable from the second optical path.

(Appended Mode 4)

The objective optical system according to appended mode 1, wherein the predetermined optical surface is positioned in the first optical path, and the optical-path splitting surface is a half-mirror surface.

(Appended Mode 5)

The objective optical system according to any one of appended modes 1 to 4, wherein the predetermined optical surface is provided with an optical film, and the optical film has spectral characteristics of generating light of the restricted wavelength band, and the following conditional expression (1) is satisfied:

$$3 \text{ nm} \leq T\lambda \times \Delta\lambda \leq 60 \text{ nm} \quad (1)$$

where, $T\lambda$ denotes the maximum transmittance ($0 \leq T\lambda \leq 1.0$) in the restricted wavelength band, and $\Delta\lambda$ denotes the full width at half maximum of the restricted wavelength band (The unit is nm).

(Appended Mode 6)

The objective optical system according to appended mode 5, wherein the number of the restricted wavelength bands is in plurality, and each of the restricted wavelength bands satisfies conditional expression (1).

(Appended Mode 7)

An endoscope apparatus, comprising:

an objective optical system according to any one of appended modes 1 to 6;

an image pickup element; and an image processing unit.

According to the present embodiment, it is possible to provide an objective optical system which enables the narrow-band light observation and the white light observation simultaneously, by using an image pickup element which is highly versatile, while being a small-sized optical system, and an endoscope apparatus using the same.

The present invention is useful for an objective optical system which enables the narrow-band light observation and the white light observation simultaneously, by using an image pickup element which is highly versatile, while being a small-sized optical system, and an endoscope apparatus using the same.

What is claimed is:

1. An objective optical system, comprising:

a lens group which forms an image of an object; and an optical-path splitting element which is disposed on an image side of the lens group, wherein:

the optical-path splitting element is disposed on an optical path of the lens group, the optical-path splitting element has an optical-path splitting surface which forms a first optical path and a second optical path, the first optical path is formed on an extended line of the optical path of the lens group, the second optical path is formed to intersect the first optical path, an optical image on the first optical path and an optical image on the second optical path are formed on a same plane, a reflecting surface is positioned in the second optical path, a predetermined optical surface is positioned in only the second optical path, a wavelength band of light transmitted through the predetermined optical surface or a wavelength band of light reflected at the predetermined optical surface is restricted, the wavelength band which is restricted is narrower than a wavelength band of light that travels along the other first optical path, a quarter-wave plate is positioned between the optical-path splitting surface and the reflecting surface, the optical-path splitting surface has a characteristic of transmitting P-polarized light and reflecting S-polarized light, the predetermined optical surface is positioned between the optical-path splitting surface and the quarter-wave plate, the predetermined optical surface is provided with an optical film, the optical film has spectral characteristics of generating light of the restricted wavelength band, and the following conditional expression (1) is satisfied:

$$3 \text{ nm} \leq T\lambda \times \Delta\lambda \leq 60 \text{ nm} \quad \text{expression (1)}$$

where, $T\lambda$ denotes the maximum transmittance $0 \leq T\lambda \leq 1.0$ in the restricted wavelength band, and $\Delta\lambda$ denotes a full width at half maximum of the restricted wavelength band.

2. An endoscope apparatus, comprising:

the objective optical system described in claim 1;

an image pickup element; and an image processing unit.

* * * * *